US011000686B1

(12) United States Patent
Yao et al.

(10) Patent No.: US 11,000,686 B1
(45) Date of Patent: May 11, 2021

(54) PLATINUM/IRIDIUM SURFACE PATTERNING BY LASER TO IMPROVE NEUROMODULATION ELECTRODE PERFORMANCE

(71) Applicant: Verily Life Sciences LLC, South San Francisco, CA (US)

(72) Inventors: Huanfen Yao, Brisbane, CA (US); Kathy Jackson, Felton, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 130 days.

(21) Appl. No.: 16/394,558

(22) Filed: Apr. 25, 2019

Related U.S. Application Data

(60) Provisional application No. 62/663,435, filed on Apr. 27, 2018.

(51) Int. Cl.
| | |
|---|---|
| *A61N 1/36* | (2006.01) |
| *H01B 1/02* | (2006.01) |
| *H05K 5/02* | (2006.01) |
| *H05K 5/00* | (2006.01) |
| *B23K 26/352* | (2014.01) |

(Continued)

(52) U.S. Cl.
CPC ....... *A61N 1/3616* (2013.01); *A61N 1/36053* (2013.01); *A61N 1/3754* (2013.01); *B23K 26/355* (2018.08); *H01B 1/02* (2013.01); *H01B 13/003* (2013.01); *H05K 5/0091* (2013.01); *H05K 5/0247* (2013.01); *C22C 5/04* (2013.01)

(58) Field of Classification Search
CPC .............. A61N 1/3516; A61N 1/36053; A61N 1/3754; B23K 26/355; H01B 1/02; H01B 13/003; H05K 5/0091; H05K 5/0247; C22C 5/04

See application file for complete search history.

(56) References Cited

U.S. PATENT DOCUMENTS

| | | |
|---|---|---|
| 7,689,260 B2 | 3/2010 | Finch et al. |
| 8,005,526 B2 | 8/2011 | Martin et al. |

(Continued)

OTHER PUBLICATIONS

Green et al., "Laser patterning of platinum electrodes for safe neurostimulation", Journal of Neural Engineering, vol. 11, No. 5, Sep. 4, 2014, 17 pages.

(Continued)

*Primary Examiner* — George Manuel
(74) *Attorney, Agent, or Firm* — Kilpatrick Townsend & Stockton LLP

(57) ABSTRACT

The present disclosure relates to neuromodulation electrodes, and in particular, to neuromodulation electrodes having a platinum/iridium surface etched with a pattern and methods of laser etching the pattern into the platinum/iridium surface of the neuromodulation electrodes to improve performance of the neuromodulation electrodes. Particularly, aspects are directed to an electrode including a base body having: (i) an interface surface that has an area of less than 50 mm², and (ii) an alloy including platinum and iridium. The interface surface has a surface topography including: (i) an artificial pattern, and (ii) a surface roughness having an arithmetical mean height ($R_a$) of greater than 0.8 μm.

19 Claims, 11 Drawing Sheets

(51) Int. Cl.
*A61N 1/375* (2006.01)
*H01B 13/00* (2006.01)
*C22C 5/04* (2006.01)

(56) References Cited

U.S. PATENT DOCUMENTS

| | | |
|---|---|---|
| 2001/0029395 A1 | 10/2001 | Stewart et al. |
| 2003/0123215 A1* | 7/2003 | Allen .................. H01G 4/35 361/302 |
| 2009/0093879 A1 | 4/2009 | Wawro et al. |
| 2010/0126404 A1 | 5/2010 | Brennan et al. |
| 2011/0301665 A1 | 12/2011 | Mercanzini et al. |
| 2014/0293384 A1* | 10/2014 | O'keeffe .................. C22C 5/02 359/2 |
| 2015/0174396 A1 | 6/2015 | Fisher et al. |
| 2018/0133457 A1 | 5/2018 | Yao et al. |

OTHER PUBLICATIONS

Ison et al., "Platinum and platinum/iridium electrode properties when used for extracochlear electrical stimulation of the totally deaf", Medical and Biological Engineering and Computing, vol. 25, Issue 4, Jul. 1987, pp. 403-413.

Petrossians et al., "Improved electrode material for deep brain stimulation", Proceedings of the 38th Annual International Conference of the IEEE Engineering in Medicine and Biology Society (EMBC), Aug. 16-20, 2016, pp. 1798-1801.

Petrossians et al., "Surface modification of neural stimulating/recording electrodes with high surface area platinum-iridium alloy coatings", Proceedings of the Annual International Conference of the IEEE Engineering in Medicine and Biology Society, Aug 30-Sep. 3, 2011, pp. 3001-3004.

PCT/US2019/044636, "International Search Report and Written Opinion", dated Oct. 25, 2019, 13 pages.

* cited by examiner

PLATINUM/IRIDIUM SURFACE PATTERNING BY LASER TO IMPROVE NEUROMODULATION ELECTRODE PERFORMANCE

CROSS-REFERENCE TO RELATED APPLICATIONS

This application claims priority to U.S. Provisional Application No. 62/663,435, filed on Apr. 27, 2018, the entirety of which is incorporated herein by reference.

FIELD OF THE INVENTION

The present disclosure relates to neuromodulation electrodes, and in particular, to neuromodulation electrodes (e.g., neurostimulation and neurorecording electrodes) having a platinum/iridium surface etched with a pattern and methods of laser etching the pattern into the platinum/iridium surface of the neuromodulation electrodes to improve performance of the neuromodulation electrodes.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems with electrode interfaces used to inject a charge into biological tissue with controlled current or voltage pulses that reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

The lead assembly of a neuromodulation device typically includes an electrically conducting wire that is insulated from the biological tissue. One end of the wire connects to a pulse generator while the other end has one or more electrodes adapted to stimulate a biological tissue, e.g., nerve or muscle fibers. Commonly used materials for fabricating electrodes for electrical stimulation of biological tissue are platinum, platinum alloys, and stainless steel. Platinum, platinum alloys and stainless steel have proven useful for such electrodes because of the high degree of bio-compatibility afforded. However, these materials are known to have a limited range for "reversible" charge injection by surface faradaic processes in an in vivo saline environment before the onset of water electrolysis and corrosion. The corrosion can cause the dissolution of trace quantities of dissolved metal into the surrounding environment, and can alter the interfacial properties between the electrode and the biological tissue. In the case of platinum or platinum alloy electrodes, dissolution products may be toxic to the biological tissue in which the electrodes are implanted. In the case of stainless steel electrodes, dissolution or corrosion of the electrodes may result in electrode failure due to corrosion-induced fracture.

In order to overcome the dissolution or corrosion problem associated with platinum and stainless steel electrodes, iridium has been used with platinum in the manufacture of the electrodes. Iridium possesses more oxidation states than platinum, and its oxide possesses a lower electrical resistance, and thus iridium shows lower electrochemical impedance over platinum. The iridium oxide essentially becomes the main charge transfer interface and enables larger charge injection densities without water electrolysis or other faradaic reactions that are involved in corrosion of platinum, platinum alloy, and stainless steel electrodes. Conventionally electrodes may be manufactured as a platinum and iridium sheet or as a thin film of platinum and iridium deposited on a metallic electrode (e.g., stainless steel) to interface with the biological tissue. Individually, platinum and iridium possess different mechanical properties. Platinum is known to be ductile and malleable, while iridium is known to be stiff and brittle. The two are often alloyed to create alloys with improved mechanical properties over the individual constituents. The exact ratio of the platinum and iridium may be adjusted so as to match the mechanical property requirements for the particular application, e.g., more platinum where a more ductile electrode is preferred and more iridium were stiffness is desired.

Although the mechanical properties of the electrodes may be adjusted for a particular application, the scale or size of many electrodes has remained relatively large, (e.g., an interface surface of greater than 50 $mm^2$), in order to maintain the surface area necessary to achieve desired charge injection densities. However, for certain neuromodulation therapies (e.g., the treatment of rheumatoid arthritis), the selectivity of therapeutic stimuli is a priority and requires targeting a relatively small tissue area for stimulation. One approach for addressing the selectivity problem may be to reduce physical dimensions of the electrodes. For example, electrodes with a smaller size (e.g., an interface surface of less than 50 $mm^2$) have the advantage of stimulating a relatively small tissue volume, which may improve selectivity of therapeutic stimuli. However, conventional electrode technology for smaller sized electrodes is associated with lower charge injection densities, inadequate impedances (impedance determines recording sensitivity), and inadequate power consumption even in instances in which the electrodes are manufactured using platinum and iridium. Accordingly, the need exists for electrodes with improved performance capabilities on the microscale level.

BRIEF SUMMARY

In various embodiments, an electrode is provided comprising a base body comprising: (i) an interface surface that has an area of less than 50 $mm^2$, and (ii) an alloy comprising platinum and iridium, wherein the interface surface has a surface topography comprising: (i) an artificial pattern, and (ii) a surface roughness having an arithmetical mean height ($R_a$) of greater than 0.8 µm.

In some embodiments, the artificial pattern comprises a plurality of trenches. Optionally, the plurality of trenches are formed as a stripe pattern. Optionally, a pitch between each trench of the plurality of trenches is between 5 µm and 100 µm.

In some embodiments, the plurality of trenches include a first set of trenches and a second set of trenches formed in a crosshatch pattern. Optionally, a pitch between each trench of the first set of trenches is between 5 µm and 100 µm, and a pitch between each trench of the second set of trenches is between 5 µm and 100 µm. Optionally, each trench of the plurality of trenches has a depth between 2 µm and 50 µm. Optionally, each trench of the plurality of trenches has a depth between 3 µm and 10 µm.

In some embodiments, the surface roughness has a $R_a$ of greater than 1.6 µm. Optionally, the surface roughness has a maximum profile valley depth ($R_v$) of greater than 1.2 µm and a maximum profile peak height ($R_p$) of greater than 1.2 µm. Optionally, the surface roughness has a total profile height ($R_t$) of greater than 2.4 µm. Optionally, the alloy comprises about 80% platinum and about 20% iridium. Optionally, the alloy comprises about 70% platinum and about 30% iridium. Optionally, the alloy comprises about 60% platinum and about 40% iridium.

In some embodiments, the electrode further comprises a charge injection capacity (Qinj) of greater than 50 µC/cm$^2$. Optionally, the charge injection capacity (Qinj) is greater than 75 µC/cm$^2$.

In some embodiments, the electrode further comprises a maximum current of greater than 5.0 mA. Optionally, the maximum current is between 10.0 mA and 15.0 mA.

In some embodiments, the electrode further comprises a maximum power consumption of less than 1.0 mW. Optionally, the maximum power consumption is less than 0.7 mW.

In various embodiments, a medical device is provided comprising: an implantable neurostimulator including: a housing; one or more feedthroughs that pass through the housing; and an electronics module within the housing and connected to the one or more feedthroughs; and a lead assembly including: a lead body including a conductor material; a lead connector that connects the conductor material to the one or more feedthroughs; and an electrode connected to the conductor material, wherein the electrode comprises: (i) an interface surface that has an area of less than 50 mm$^2$, and (ii) an alloy comprising platinum and iridium, wherein the interface surface has a surface topography comprising: (i) an artificial pattern, and (ii) a surface roughness having an arithmetical mean height ($R_a$) of greater than 0.8 µm.

In some embodiments, the artificial pattern comprises a plurality of trenches. Optionally, the plurality of trenches are formed as a stripe pattern. Optionally, a pitch between each trench of the plurality of trenches is between 5 µm and 100 µm. Optionally, the plurality of trenches include a first set of trenches and a second set of trenches formed in a crosshatch pattern. Optionally, a pitch between each trench of the first set of trenches is between 5 µm and 100 µm, and a pitch between each trench of the second set of trenches is between 5 µm and 100 µm.

In some embodiments, each trench of the plurality of trenches has a depth between 2 µm and 50 µm. Optionally, each trench of the plurality of trenches has a depth between 3 µm and 10 µm.

In some embodiments, the surface roughness has a $R_a$ of greater than 1.6 µm. Optionally, the surface roughness has a maximum profile valley depth ($R_v$) of greater than 1.2 µm and a maximum profile peak height ($R_p$) of greater than 1.2 µm. Optionally, the surface roughness has a total profile height ($R_t$) of greater than 2.4 µm. Optionally, the alloy comprises about 80% platinum and about 20% iridium. Optionally, the alloy comprises about 70% platinum and about 30% iridium. Optionally, the alloy comprises about 60% platinum and about 40% iridium.

In some embodiments, the electrode further comprises a charge injection capacity (Qinj) of greater than 50 µC/cm$^2$. Optionally, the charge injection capacity (Qinj) is greater than 75 µC/cm$^2$.

In some embodiments, the electrode further comprises a maximum current of greater than 5.0 mA. Optionally, the maximum current is between 10.0 mA and 15.0 mA.

In some embodiments, the electrode further comprises a maximum power consumption of less than 1.0 mW. Optionally, the maximum power consumption is less than 0.7 mW.

In various embodiments, a method of manufacturing an electrode is provided comprising: obtaining a base body comprising (i) an interface surface that has an area of less than 50 mm$^2$, and (ii) an alloy comprising platinum and iridium; and surface texturing, using a laser device, at least a portion of the interface surface to create a surface topography comprising: (i) an artificial pattern, and (ii) a surface roughness having an arithmetical mean height ($R_a$) of greater than 0.8 µm.

In some embodiments, the portion comprises at least 50% of the interface surface. Optionally, the portion comprises at least 80% of the interface surface. Optionally, the surface texturing comprises using a direct beam to create the artificial pattern. Optionally, the surface texturing comprises using a scanning system to create the artificial pattern. Optionally, the artificial pattern comprises a plurality of microcavities. Optionally, the surface texturing comprises using an interference pattern to create the artificial pattern. Optionally, the artificial pattern comprises a plurality of trenches. Optionally, the plurality of trenches are formed as a stripe pattern.

In some embodiments, a pitch between each trench of the plurality of trenches is between 5 µm and 100 µm. Optionally, the plurality of trenches include a first set of trenches and a second set of trenches formed in a crosshatch pattern. Optionally, a pitch between each trench of the first set of trenches is between 5 µm and 100 µm, and a pitch between each trench of the second set of trenches is between 5 µm and 100 µm. Optionally, each trench of the plurality of trenches has a depth between 3 µm and 10 µm. Optionally, each trench of the plurality of trenches has a depth between 5 µm and 7 µm.

In some embodiments, the surface roughness has a $R_a$ of greater than 1.6 µm. Optionally, the surface roughness has a maximum profile valley depth ($R_v$) of greater than 1.2 µm and a maximum profile peak height ($R_p$) of greater than 1.2 µm. Optionally, the surface roughness has a total profile height ($R_t$) of greater than 2.4 µm. Optionally, the alloy comprises about 80% platinum and about 20% iridium. Optionally, the alloy comprises about 70% platinum and about 30% iridium. Optionally, the alloy comprises about 60% platinum and about 40% iridium.

BRIEF DESCRIPTION OF THE DRAWINGS

The present invention will be better understood in view of the following non-limiting figures, in which.

DETAILED DESCRIPTION

I. Introduction

Figure 1A:
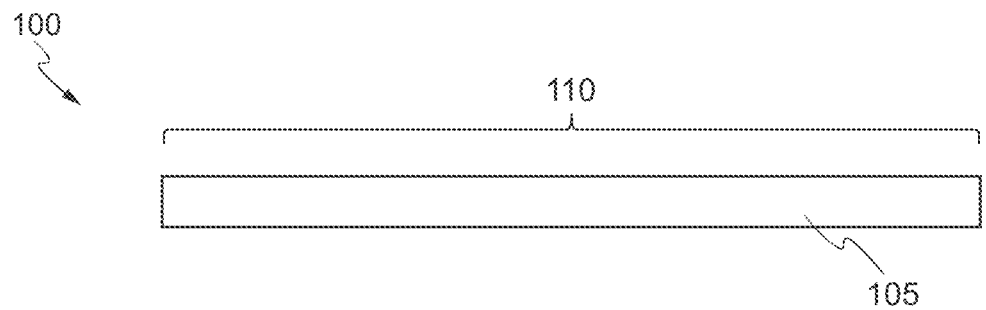
FIGS. 1A-1O show electrodes in accordance with various embodiments.

The following disclosure describes neuromodulation electrodes having a platinum/iridium surface etched with a pattern and methods of laser etching the pattern into the platinum/iridium surface of the neuromodulation electrodes to improve performance of the neuromodulation electrodes. As used herein, the phrase "neuromodulation electrode" or "electrode" refers to an electrode (recording or stimulation) with an interface surface having an area of less than 50 mm². The area of the interface surface is an expression of the size of a 2-dimensional plane. As used herein, the phrase "interface surface" refers to a surface forming a common boundary of the electrode and the biological tissue. In various embodiments, an electrode is provided comprising a base body comprising: (i) an interface surface that has an area of less than 50 mm², and (ii) an alloy comprising platinum and iridium.

In some embodiments, the interface surface has a predetermined surface topography. Surface topography is the local deviations of a surface from a perfectly flat plane, and may be defined by the three characteristics of lay, surface roughness, and waviness. Lay is the direction of the predominant surface pattern, ordinarily determined by the production method used. Surface roughness is a measure of the finely spaced surface irregularities. Waviness is the measure of surface irregularities with a spacing greater than that of surface roughness. These irregularities usually occur due to warping, vibrations, or deflection during machining.

Parameters for surface roughness (also described herein as roughness) can either be calculated on a profile (line) or on a surface (area). Each of the roughness parameters are calculated using a formula for describing the surface. The profile roughness parameters are included in BS EN ISO 4287:2000 British Standard, identical with the ISO standard 4287:1997, which is based on the mean line system. The profile roughness parameters include an arithmetical mean height ($R_a$), a maximum profile valley depth ($R_v$), a maximum profile peak height ($R_p$), and a total profile height ($R_t$). $R_a$ is the arithmetic average of the absolute values of the profile height deviations from the mean line, recorded within the evaluation length. $R_t$ is the vertical distance between the $R_p$ and the $R_v$ along the evaluation length. $R_v$ indicates the point along the sampling length at which the profile curve is lowest. $R_p$ indicates the point along the sampling length at which the curve is highest. The profile roughness parameters may be measured using a contact technique such as use of a profilometer or noncontact technique such as use of an electron microscope.

A problem associated with conventional electrodes is that the interface surface is substantially a flat plane (absence of a surface topography). Despite the often nanoscale nature of surface irregularities, the influence the surface irregularities have on an object may be observed by macroscopic measurements. For example, the presence or absence of a topography of a surface is known to substantially affect the intensive or bulk properties of a material. More recently, it has been discovered that the presence or absence of a topography of an electrode surface can substantially affect the ability of the electrode to inject a charge into biological tissue with controlled current or voltage pulses. In particular, it has been found that the substantially flat plane interface surface of a conventional electrode typically results in a lower than optimal charge injection density and a high impedance that ultimately causes high power consumption.

Conventional electrode manufacturing processes such as the application of metal coatings to base electrodes may create a minor topography for the interface surface (e.g., minor irregularities in the interface surface) of the electrode. However, these conventional processes have low repeatability, low robustness, and introduce increased complexity into the electrode manufacturing process, which result in a minor surface topography that suffers from similar problems as the flat plane electrodes (i.e., lower than optimal charge injection density and a high impedance that ultimately causes high power consumption). As used herein, the phrase "minor surface topography" refers to a topography with no predominant lay (e.g., no pattern) and a surface roughness with an arithmetical mean height ($R_a$) of less than 0.8 μm.

To address these problems, the interface surface of various embodiments disclosed herein has a predetermined surface topography comprising: (i) an artificial pattern, and (ii) a surface roughness having an arithmetical mean height ($R_a$) of greater than 0.8 μm. As used herein, the phrase "artificial pattern" refers to a pattern that is intentionally created by a well-controlled and robust manufacturing process, such as laser etching. One illustrative embodiment of the present disclosure comprises: an electrode comprising a base body comprising: (i) an interface surface that is less than 50 mm², and (ii) an alloy comprising platinum and iridium, wherein the interface surface has a surface topography comprising: (i) an artificial pattern, and (ii) a surface roughness having an arithmetical mean height ($R_a$) of greater than 0.8 μm. In some embodiments, the surface roughness has a maximum profile valley depth ($R_v$) of greater than 1.2 μm and a maximum profile peak height ($R_p$) of greater than 1.2 μm. Another illustrative embodiment of the present disclosure comprises: a method of manufacturing an electrode, comprising: obtaining a base body comprising (i) an interface surface that is less than 50 mm², and (ii) an alloy comprising platinum and iridium; and surface texturing, using a laser, at least a portion of the interface surface to create a surface topography comprising: (i) an artificial pattern, and (ii) a surface roughness having an arithmetical mean height ($R_a$) of greater than 0.8 μm. In some embodiments, the portion comprises at least 80% of the interface surface, and the surface roughness has a maximum profile valley depth ($R_v$) of greater than 1.2 μm and a maximum profile peak height ($R_p$) of greater than 1.2 μm.

Advantageously, these approaches provide an electrode that has increased selectivity of therapeutic stimuli since the electrode is small enough to target a relatively small tissue area for stimulation. Moreover, these approaches allow the electrode to achieve high charge injection density while maintaining low impedance, and consequently low power consumption. Also advantageously, these approaches provide for a controlled and robust manufacturing process to be used in the manufacture of the electrode.

II. Electrodes for a Neuromodulation System

Figure 1B:
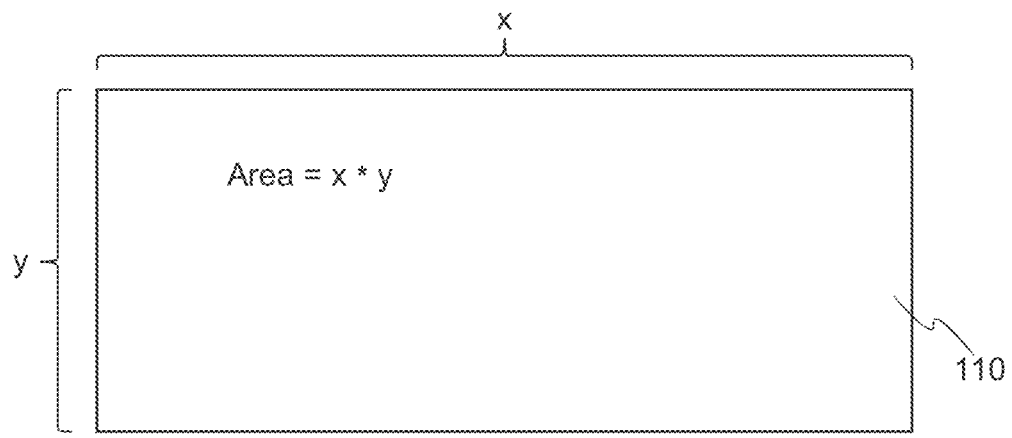
Figure 1C:
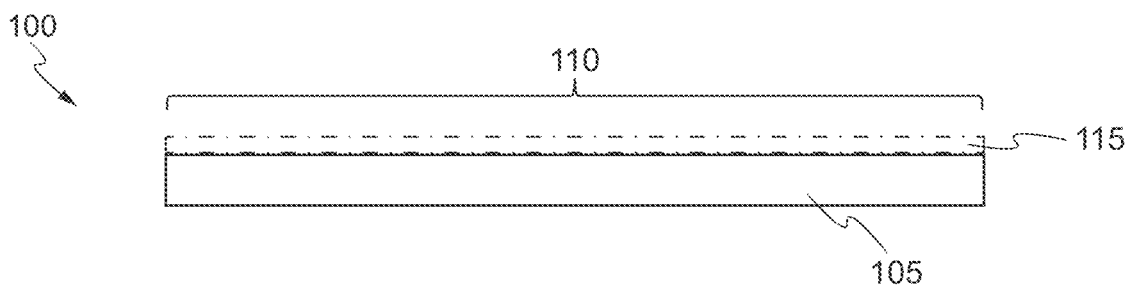
Figure 1D:
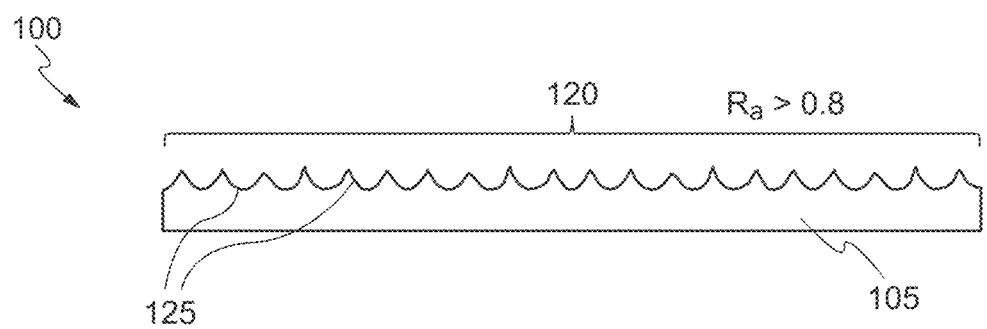
Figure 1E:
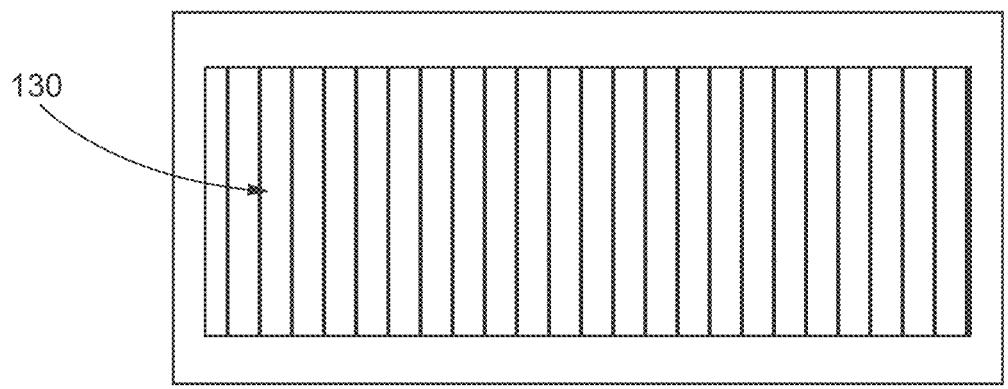
Figure 1F:
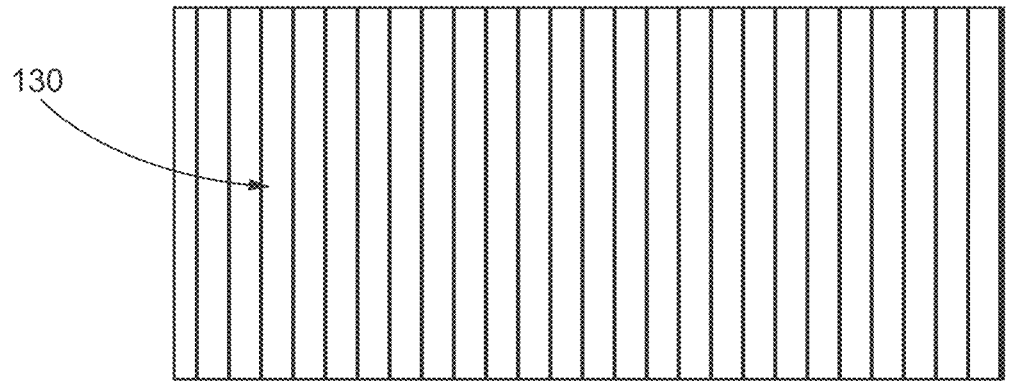
Figure 1G:
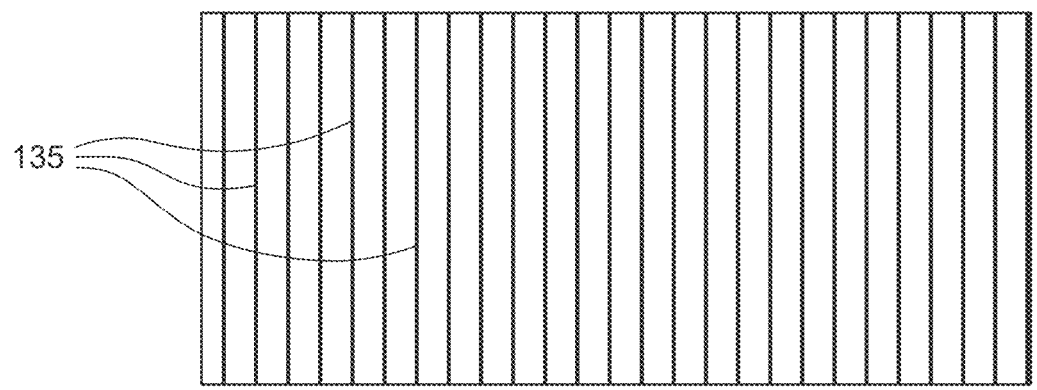
Figure 1H:
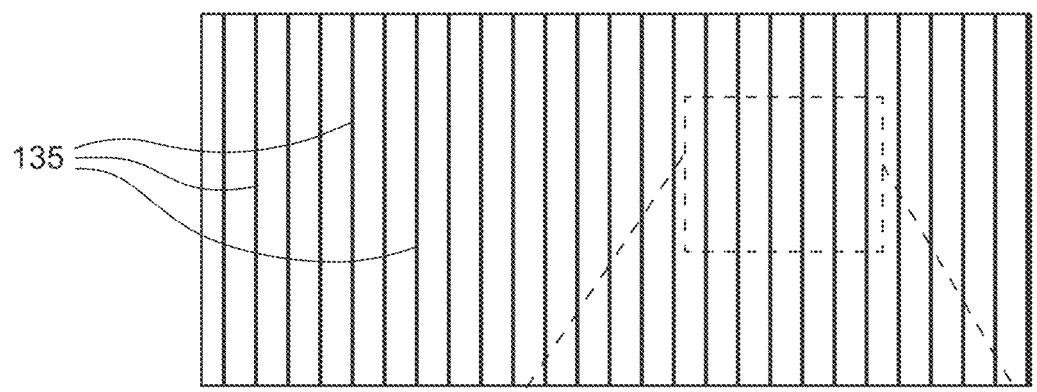
Figure 1H:
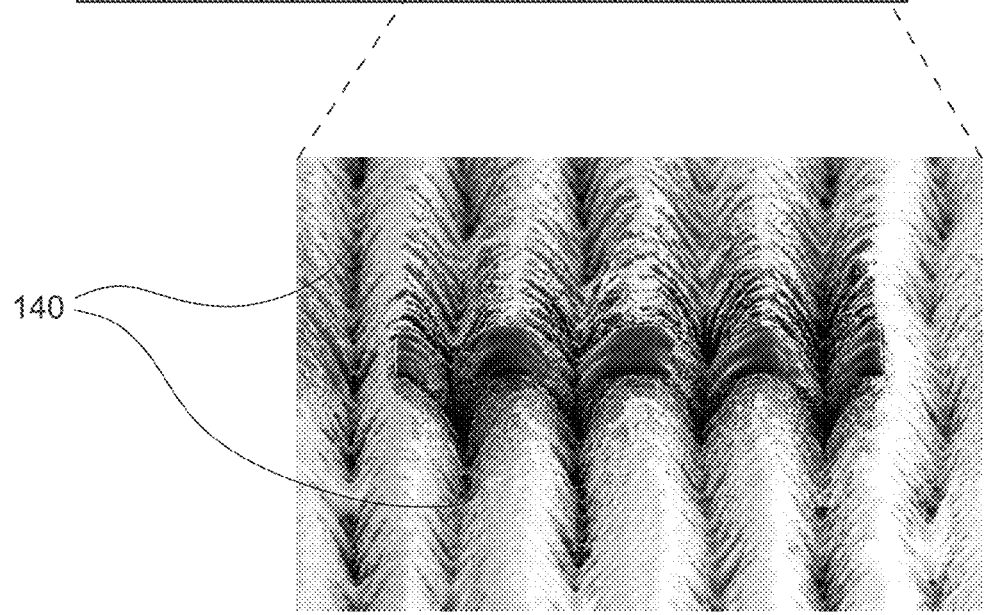
Figure 1I:
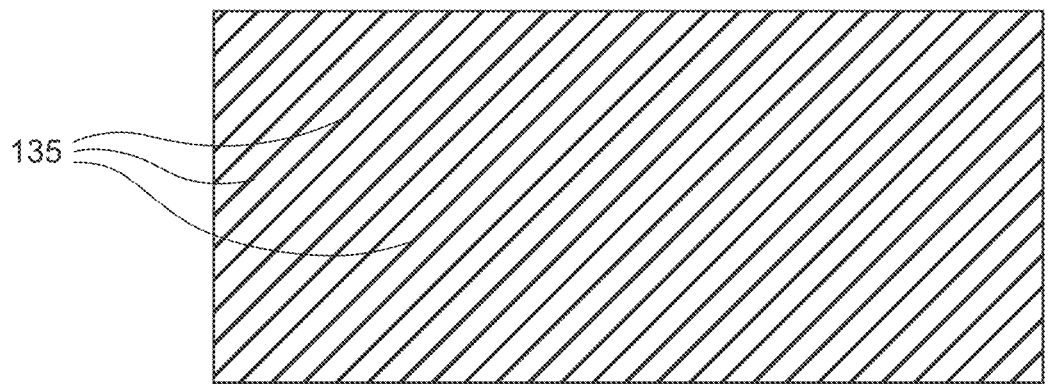
Figure 1J:
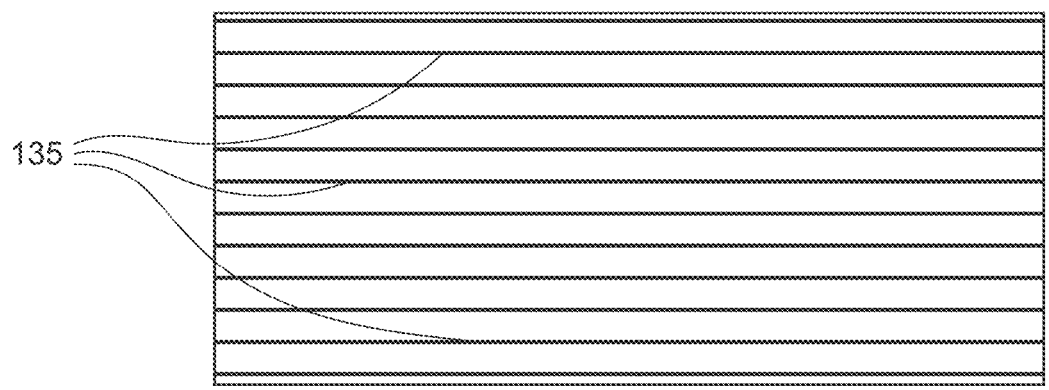
Figure 1K:
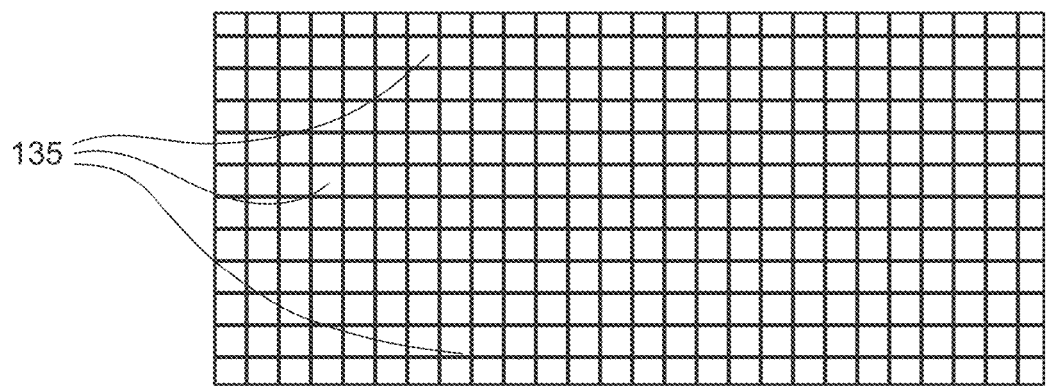
Figure 1L:
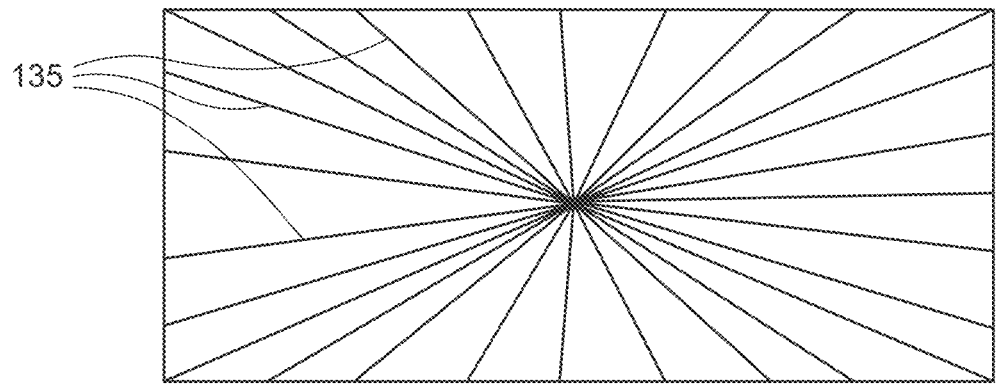
Figure 1M:
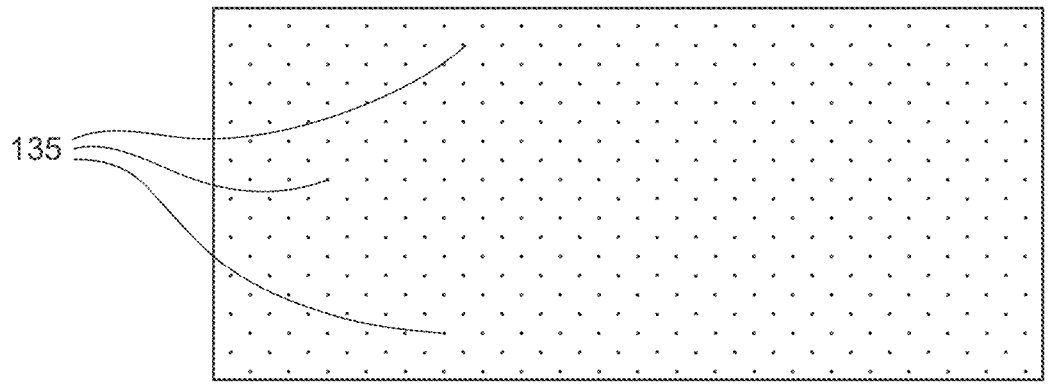
Figure 1N:
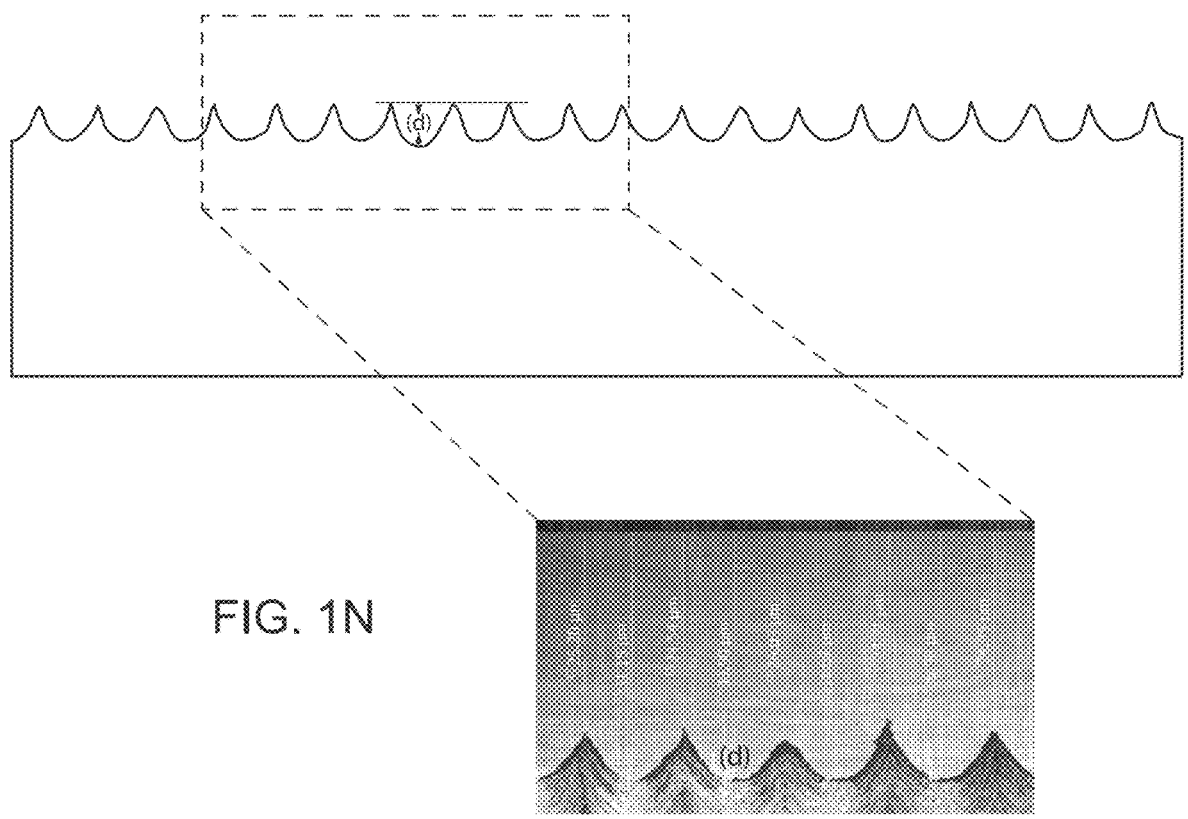
Figure 1O:
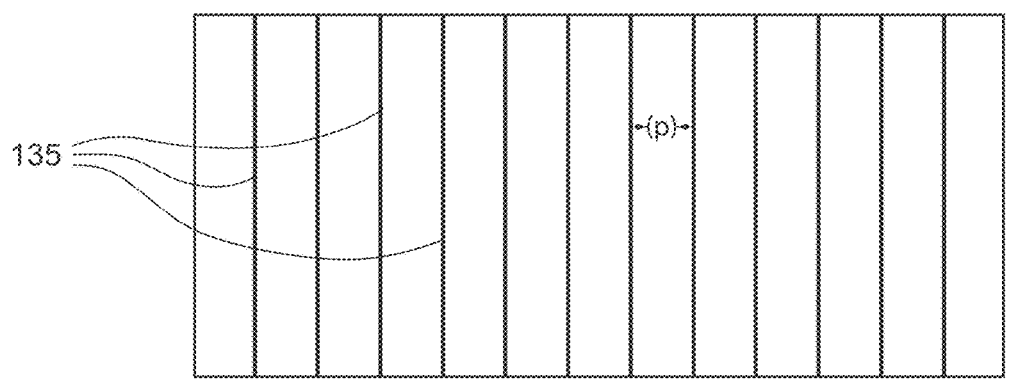

FIGS. 1A-1O show electrodes 100 comprising a base body 105. In various embodiments, the base body comprises: (i) an interface surface 110 that has an area of less than 50 mm², and (ii) an alloy comprising platinum and iridium, as shown in FIGS. 1A and 1B. In some embodiments, the base body may further comprise (iii) a coating layer 115 comprising a metal, alloy, or oxide, for example an iridium oxide, as shown in FIG. 1C. In other embodiments, the alloy is a stainless steel alloy. In other embodiments, the alloy is a stainless steel alloy and the coating layer 115 is an alloy comprising platinum and iridium. In other embodiments, the base body 105 comprises titanium, tantalum, platinum, iridium, alloys of titanium, alloys of tantalum, alloys of platinum, alloys of iridium, or combinations thereof. In some embodiments, the base body 105 has a thickness of 0.5 µm to 100.0 µm, for example between 2.0 µm and 25.0 µm or between 2.0 µm and 5.0 µm. In some embodiments, the coating layer 115 has a thickness of 0.1 µm to 1.5 µm, for example between 0.2 µm and 0.7 µm.

In various embodiments, the interface surface 110 has an area of less than 50 mm$^2$, for example from 4.0 mm$^2$ to 20.0 mm$^2$. In other embodiments, the interface surface 110 has an area of less than 25 mm$^2$, for example from 0.5 mm$^2$ to 7 mm$^2$. In some embodiments, the alloy comprises about 90% platinum and about 10% iridium. In other embodiments, the alloy comprises about 80% platinum and about 20% iridium. In other embodiments, the alloy comprises about 70% platinum and about 30% iridium. In other embodiments, the alloy comprises about 60% platinum and about 40% iridium. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

In various embodiments, the interface surface 110 has a surface topography 120 comprising: (i) an artificial pattern 125, and (ii) a surface roughness having an arithmetical mean height ($R_a$) of greater than 0.8 µm, as shown in FIG. 1D. The surface topography 120 may be created by one or more manufacturing processes (discussed in detail herein) on at least a portion 130 of the interface surface 110, as shown in FIG. 1E. In some embodiments, the portion 130 comprises at least 50% of the interface surface 110, for example, between about 55% and about 85% of the interface surface 110. In other embodiments, the portion 130 comprises at least 80% of the interface surface 110, for example, between about 85% and about 98% of the interface surface 110. In some embodiments, the portion 130 comprises 100% of the interface surface 110 or covers the entirety of the interface surface 110, as shown in FIG. 1F.

In various embodiments, the artificial pattern 125 comprises a plurality of features 135, as shown in FIG. 1G. The features 135 may be trenches, dimples, channels, etc. In some embodiments, the features 135 are trenches 140, as shown in FIG. 1H. In other embodiments, the plurality of features 135 are dimples. In other embodiments, the plurality of features 135 are trenches, dimples, channels, or a combination thereof. The plurality of features 135 may be provided as a parallel pattern, a perpendicular pattern, a crosshatch pattern, a multi-directional pattern, a circular pattern, a radial pattern, or a particulate pattern. In some embodiments, the plurality of features 135 are trenches provided as a parallel pattern, as shown in FIGS. 1G, 1I, and 1J. In other embodiments, the plurality of features 135 are trenches provided as a crosshatch pattern, as shown in FIG. 1K. In other embodiments, the plurality of features 135 are trenches provided as a radial pattern, as shown in FIG. 1L. In other embodiments, the plurality of features 135 are dimples provided as a particulate pattern, as shown in FIG. 1M.

In various embodiments, the plurality of features 135 have a depth (d), as shown in FIG. 1N. As used herein, the term "depth" refers to a maximum depth of a feature or a plurality of features. The depth (d) is greater than 1.5 µm, for example between 2 µm and 50 µm, and may be substantially the same for all of the plurality of features 135 or may vary for some or each of the plurality of features 135. In some embodiments, each feature 135 of the plurality of features 135 has a depth between 3 µm and 10 µm. In other embodiments, each feature 135 of the plurality of features 135 has a depth between 5 µm and 7 µm. In other embodiments, each feature 135 of the plurality of features 135 has a depth of about 5 µm. In various embodiments, a first set of features 135(a) have a first depth (d1) and a second set of features 135(b) have a second depth (d2). In some embodiments, a first set of features 135(a) and a second set of features 135(b) have a same depth (d).

In various embodiments, the plurality of features 135 have a pitch (p), as shown in FIG. 1O. As used herein, the term "pitch" refers to a minimum distance between adjacent features of the plurality of features. The pitch (p) is greater than 2 µm, for example between 3 µm and 150 µm, and may be substantially the same between all of the plurality of features 135 or may vary between some or each of the plurality of features 135. In some embodiments, each feature 135 of the plurality of features 135 has a depth between 3 µm and 10 µm. In other embodiments, a pitch (p) between each feature 135 of the plurality of features 135 is between 5 µm and 100 µm. In other embodiments, a pitch (p) between each feature 135 of the plurality of features 135 is about 5 µm. In various embodiments, a first set of features 135(a) have a first pitch (p1) between each feature 135(a) that is between 5 µm and 100 µm and a second set of features 135(b) have a second pitch (p2) between each feature 135(b) that is between 5 µm and 100 µm. In some embodiments, a first set of features 135(a) and a second set of features 135(b) have a same pitch (p).

Figure 2A:
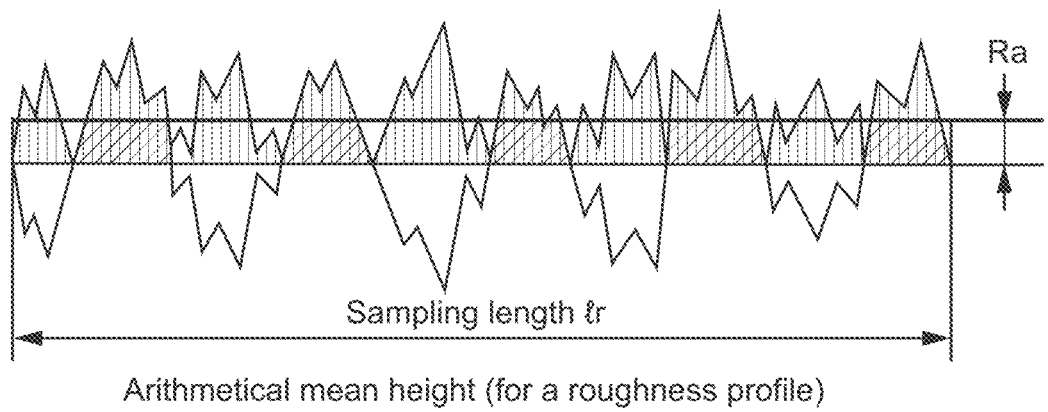
FIGS. 2A-2D show profile roughness parameters in accordance with various embodiments.
Figure 2B:
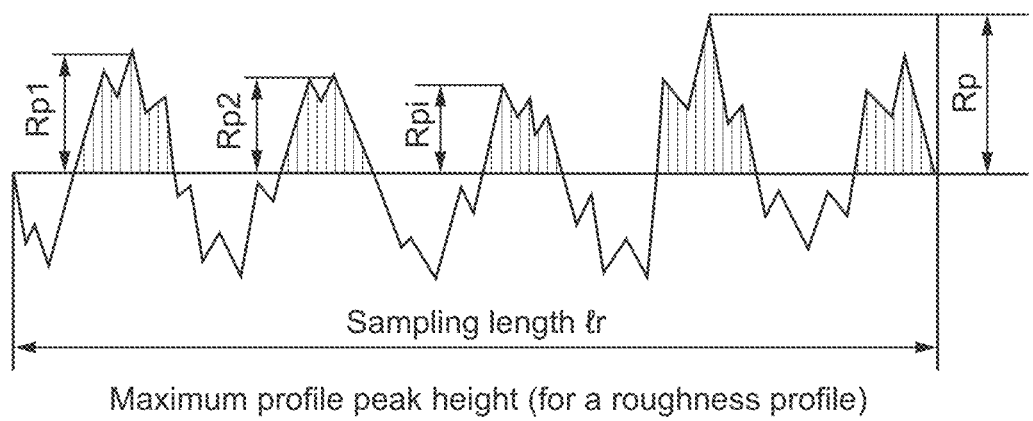
Figure 2C:
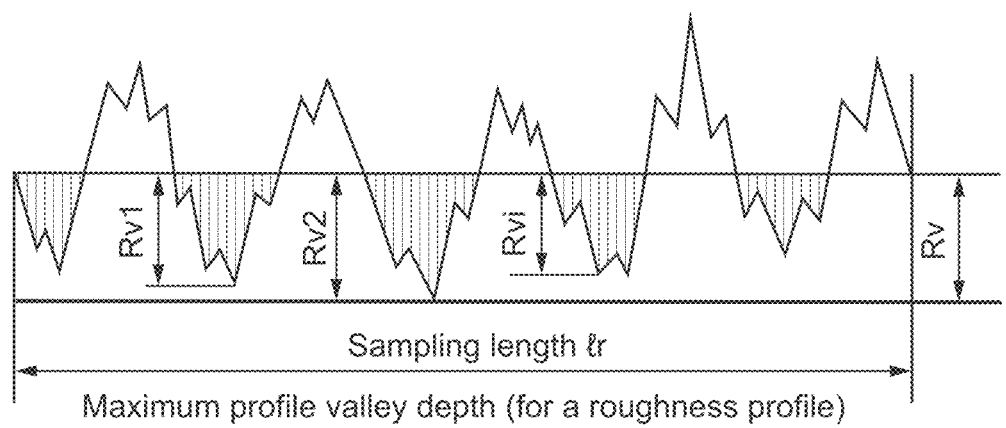
Figure 2D:
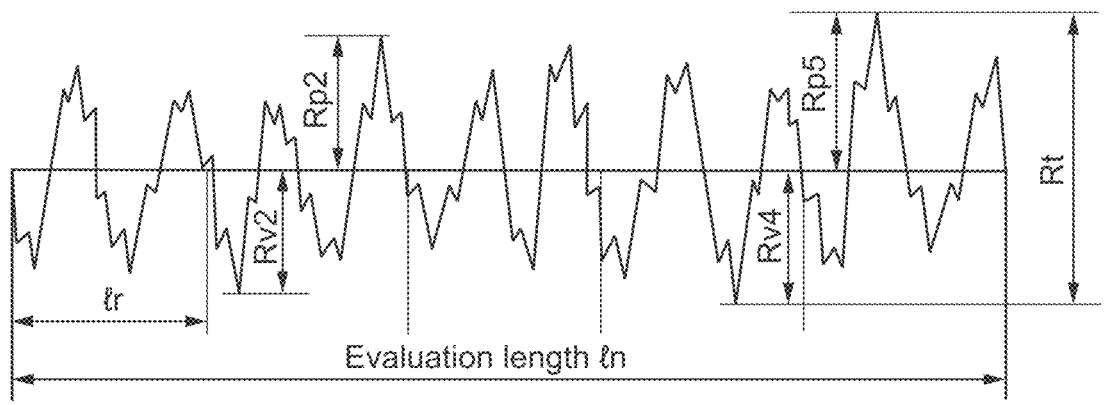

In various embodiments, the surface roughness has an arithmetical mean height ($R_a$) of greater than 0.8 µm, as shown in FIG. 2A. In some embodiments, the surface roughness has an $R_a$ of greater than 1.6 µm, for example between 1.8 µm and 50 µm. In certain embodiments, the surface roughness has a $R_a$ of between 0.9 µm and 1.6 µm. In other embodiments, the surface roughness has a $R_a$ of between 0.9 µm and 4.5 µm. In various embodiments, the surface roughness has a maximum profile peak height ($R_p$) of greater than 1.2 µm, as shown in FIG. 2B. In some embodiments, the surface roughness has an $R_p$ of greater than 2.0 µm, for example between 2.1 µm and 4.5 µm. In some embodiments, the surface roughness has an $R_p$ of less than 5.0 µm. In various embodiments, the surface roughness has a maximum profile valley depth ($R_v$) of greater than 1.2 µm, as shown in FIG. 2C. In some embodiments, the surface roughness has an $R_v$ of greater than 2.0 µm, for example between 2.1 µm and 4.5 µm. In various embodiments, the surface roughness has total profile height ($R_t$) of greater than 2.4 µm, as shown in FIG. 2D. In some embodiments, the surface roughness has an $R_t$ of greater than 4.0 µm, for example between 4.2 µm and 9.0 µm. In some embodiments, the surface roughness has an $R_t$ between 4.2 µm and 8.5 µm.

Figure 3:
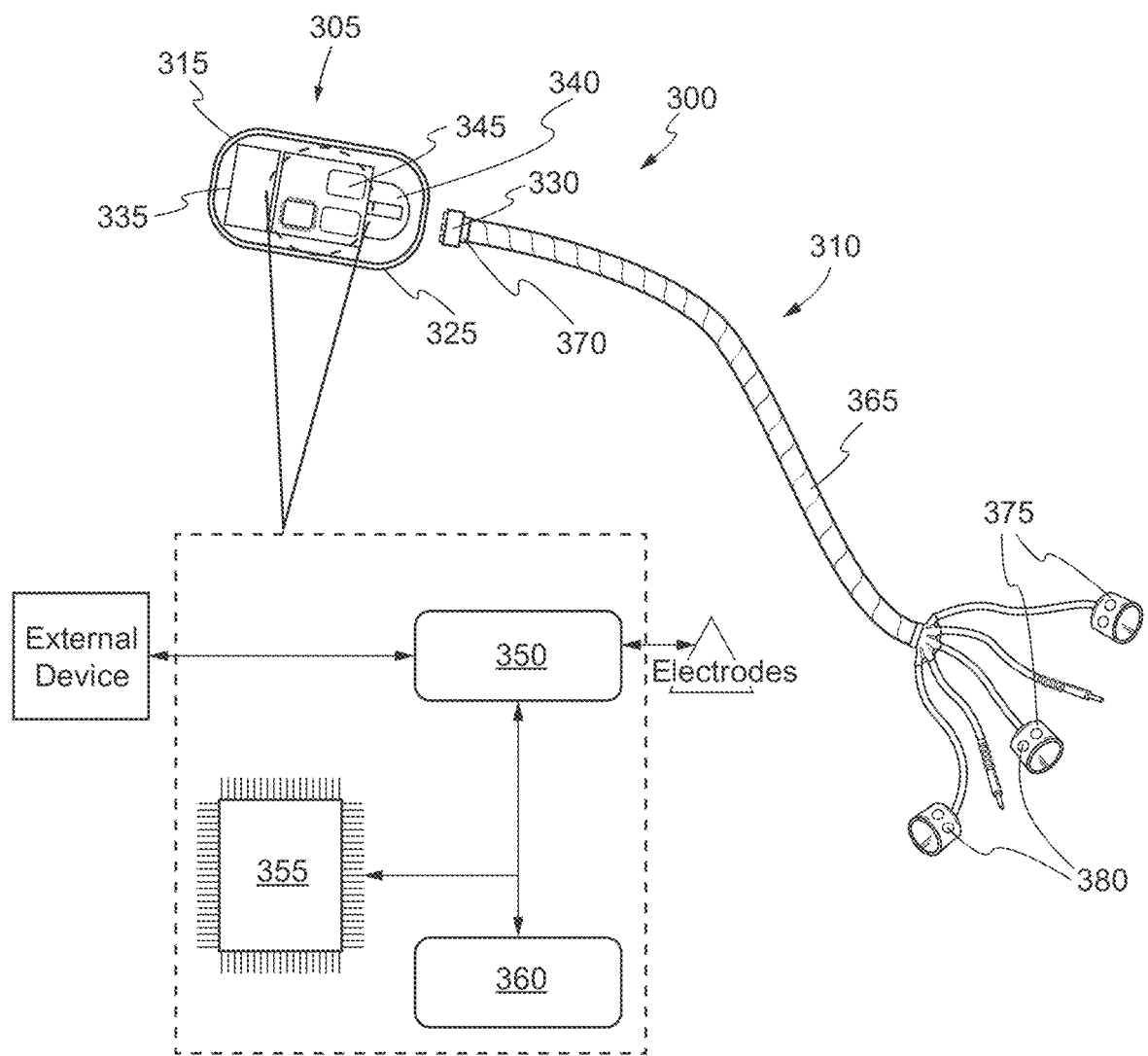
FIG. 3 shows a neuromodulation system in accordance with various embodiments.

FIG. 3 shows a neuromodulation system 300 for injecting a charge into a target biological tissue in accordance with various aspects. In some embodiments, the neuromodulation system 300 includes an implantable neurostimulator 305 and a lead assembly 310. In certain embodiments, the implantable neurostimulator 305 includes a housing 315, a feedthrough assembly 330, a power source 335, an antenna 340, and an electronics module 345 (e.g., a computing system). The housing 315 may be comprised of materials that are biocompatible such as bioceramics or bioglasses for radio frequency transparency, or metals such as titanium.

The feedthrough assembly 330 may be attached to a hole in a surface of the housing 315 such that the housing 315 is hermetically sealed. The feedthrough assembly 330 may include one or more feedthroughs (i.e., electrically conductive elements, pins, wires, tabs, pads, etc.) mounted within and extending through the surface of the housing 315 or a cap from an interior to an exterior of the housing 315. The power source 335 may be within the housing 315 and connected (e.g., electrically connected) to the electronics module 345 to power and operate the components of the electronics module 345. The antenna 340 may be connected (e.g., electrically connected) to the electronics module 345 for wireless communication with external devices via, for example, radiofrequency (RF) telemetry.

In some embodiments, the electronics module 345 is connected (e.g., electrically connected) to interior ends of the feedthrough assembly 330 such that the electronics module 345 is able to apply a signal or electrical current to leads of the lead assembly 310 connected to exterior ends of the feedthrough assembly 330. The electronics module 345 includes discrete and/or integrated electronic circuit components that implement analog and/or digital circuits capable of producing the functions attributed to the neuromodulation devices or systems. In certain embodiments, the electronics module 345 includes software and/or electronic circuit components such as a pulse generator 350 that generates a signal to deliver a voltage, current, optical, or ultrasonic stimulation to a nerve or artery/nerve plexus via electrodes, a controller 355 that determines, senses or records electrical activity and physiological responses via the electrodes and optionally sensors (e.g., a blood pressure sensor), controls stimulation parameters of the pulse generator 350 (e.g., control stimulation parameters based on feedback from the physiological responses) and causes on-demand delivery of the stimulation via the pulse generator 350 and electrodes, and a memory 360 with program instructions operable on by the pulse generator 350 and the controller 355 to perform one or more processes for delivering neurostimulation.

In various embodiments, the lead assembly 310 includes a lead body 365, a lead connector 370, and one or more electrode assemblies 375. In some embodiments, the lead connector 370 is bonding material that bonds conductor material of the lead body 365 to the electronics module 345 of the implantable neurostimulator 315 via the feedthrough assembly 330. The bonding material may be a conductive epoxy or a metallic solder or weld such as platinum. In other embodiments, the lead connector 370 is conductive wire or tab (e.g., a wire or tab formed of copper, silver, or gold) that bonds conductor material of the lead body 365 to the electronics module 345 of the implantable neurostimulator 305. In alternative embodiments, the implantable neurostimulator 305 and the lead body 365 may be designed to connect with one another via a lead connector 370 such as a pin and sleeve connector, snap and lock connector, flexible printed circuit connectors, or other means known to those of ordinary skill in the art.

The lead body 365 may include one or more leads of conductive material and insulator. The one or more leads carry electrical conductors that allow electrical coupling of the electronics module 345 to electrodes 380 of the one or more electrode assemblies 375 via the lead connector 370. In some examples the one or more leads are extruded with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends can be used. In some embodiments, the conductive material for the one or more leads may serve as a strengthening member onto which the body of the lead is extruded. For example, a distal electrode may couple to a centrally located wire on which the body of lead is extruded. The conductive material may be any suitable conductor such as stainless steel, silver, copper or other conductive materials, which may have separate coatings or sheathing for anticorrosive, insulative and/or protective reasons. The conductive material may take various forms including wires, drawn filled tubes, helical coiled conductors, microwires, and/or printed circuits, for example.

In various embodiments, the electrodes 380 are formed as discussed herein with respect to FIGS. 1A-1O and 2A-2D. For example, one or more of the electrodes 380 comprises: (i) an interface surface that has an area of less than 50 mm$^2$, and (ii) an alloy comprising platinum and iridium, wherein the interface surface has a surface topography comprising: (i) an artificial pattern, and (ii) a surface roughness having an arithmetical mean height ($R_a$) of greater than 0.8 µm. These approaches allow the one or more electrodes 380 (connected electrically to electronics module 345) to achieve a high charge injection density while maintaining low impedance, and consequently low power consumption. In some embodiments, the one or more electrodes 380 further comprise a charge injection capacity (Qinj) of greater than 50 µC/cm$^2$. In other embodiments, the one or more electrodes 380 further comprise a charge injection capacity (Qinj) of greater than 75 µC/cm$^2$, for example between 80 µC/cm$^2$ and 100 µC/cm$^2$. In some embodiments, the one or more electrodes 380 further comprise a maximum current of greater than 5.0 mA. In other embodiments, the one or more electrodes 380 further comprise a maximum current of between 10.0 mA and 15.0 mA. In some embodiments, the one or more electrodes 380 further comprise a maximum power consumption of less than 1.0 mW. In other embodiments, the one or more electrodes 380 further comprise a maximum power consumption of less than 0.7 mW.

III. Methods of Manufacturing an Electrode

Figure 4:
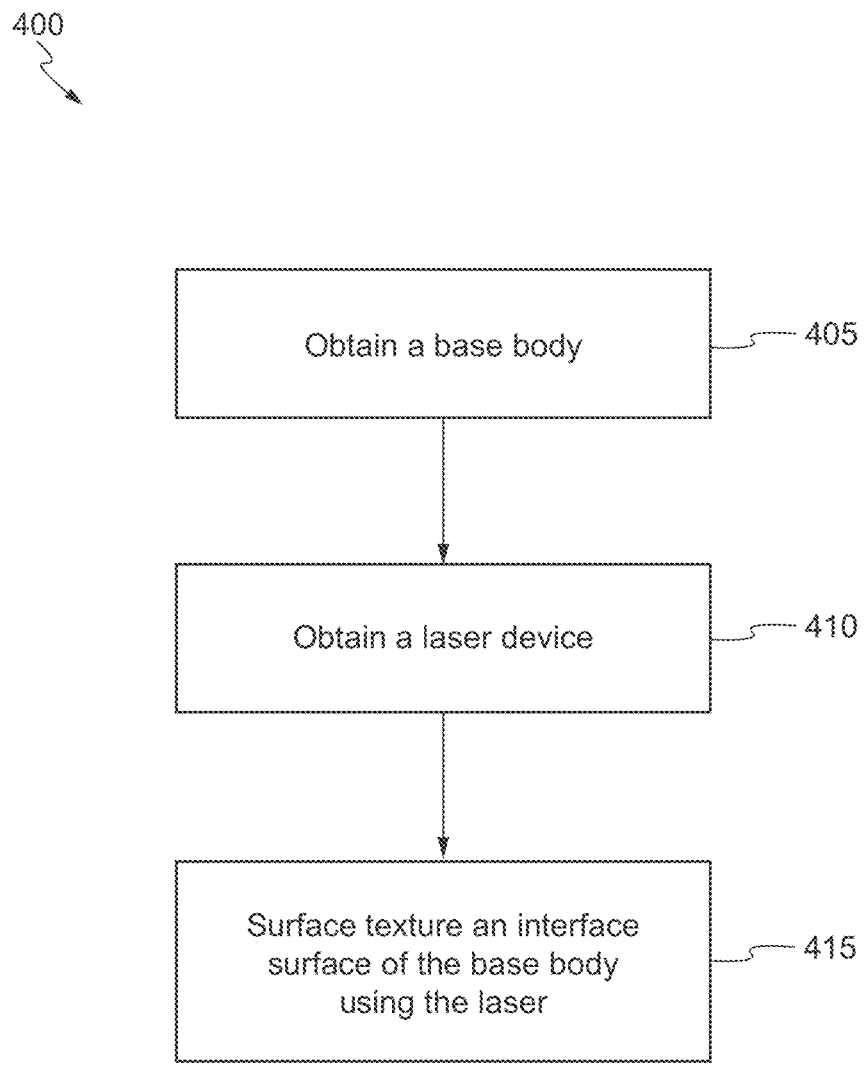
FIG. 4 shows an exemplary flow for manufacturing an electrode in accordance with various embodiments.

FIG. 4 depicts a simplified flowchart 400 depicting processing to manufacture an electrode according to various embodiments. As noted herein, the flowchart 400 of FIG. 4 illustrates the architecture, functionality, and operation of possible implementations of systems, methods, and computer program products according to various embodiments of the present invention. In this regard, each block in the flowchart 400 or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented manually by a user such as an engineer or by special purpose hardware-based systems that perform the specified functions or acts, or combinations of special purpose hardware and computer instructions.

In some embodiments, the electrode is manufactured to include features as described with respect to FIGS. 1A-1O, 2A-2D, and 3. In step 405, a base body is obtained. In various embodiments, the base body may be manufactured using processes know in the art, or may be obtained premanufactured. In various embodiments, the base body comprises (i) an interface surface that has an area of less than 50 mm$^2$, and (ii) an alloy comprising platinum and iridium. At step 410, a laser device is obtained. In various embodiments, the laser device is capable of: generating a pulsed or continuous wave light beam having a predetermined profile (e.g., a substantially Gaussian radial profile), moving at a selected speed relative to the interface surface to be etched, and discontinuously or continuously activating with a selected power density and selected beam parameters.

At step 415, surface texturing is applied using the laser device to at least a portion of the interface surface of the base body to create a surface topography. In various embodiments, the surface topography comprises: (i) an artificial pattern, and (ii) a surface roughness having an arithmetical mean height ($R_a$) of greater than 0.8 μm. In some embodiments, the surface texturing comprises actuating the laser device, directing the pulsed or continuous wave light beam on the interface surface and moving the laser beam at a predetermined speed relative to interface surface in order to etch a plurality of features (e.g., V-shaped trench) therein in an artificial pattern having a predetermined length, depth, width, and pitch. The surface texturing may comprise using a direct beam or a scanning system to create the artificial pattern. In certain embodiments, the artificial pattern comprises a plurality of microcavities (e.g., dimples created by pulsing the laser device). The surface texturing may comprise using an interference pattern to create the artificial pattern. In certain embodiments, the artificial pattern comprises a plurality of trenches (e.g., V-shaped trenches created by a continuous moving laser). In some embodiments, the surface texturing comprises actuating the laser device, directing the pulsed or continuous wave light beam on the interface surface and moving the laser beam at a predetermined speed relative to interface surface in order to create a surface topography with a predetermined lay roughness. The predetermined lay may be an artificial pattern having a predetermined length, depth, width, and pitch. The predetermined roughness may comprise one or more profile roughness parameters, for example, an $R_v$ of greater than 1.2 μm and a $R_p$ of greater than 1.2 μm.

IV. Examples

Without intending to limit the scope of the embodiments discussed herein, the systems and methods implemented in various embodiments may be better understood by referring to the following examples.

EXAMPLE 1: The performance of an embodiment of an electrode (A) was evaluated versus a control electrode (B). The electrode (A) was manufactured in accordance with the processes described with respect to FIG. 4. The electrode (A) comprised: (i) an interface surface that has an area of 6.48 mm$^2$, and (ii) an alloy comprising platinum and iridium. The interface surface had a surface topography comprising: (i) a horizontal stripe pattern, and (ii) a surface roughness having a $R_a$ of about 1.0 μm. The control electrode (B) comprised: (i) an interface surface that had an area of 4.00 mm$^2$, and (ii) an alloy comprising platinum and iridium. The interface surface had a surface topography comprising: (i) substantially a flat plane, and (ii) a surface roughness having a $R_a$ of about 0.2 μm. As shown in Table 1, the electrode (A) outperformed the control electrode (B). In particular, the electrode (A) showed a higher charge injection density while maintaining low impedance, and consequently low power consumption, as compared to the control electrode (B). The maximum current was obtained by voltage transient testing, which included applying biphasic current pulses with symmetric charge balanced current pulses (negative current first and positive current next). The voltage responses were measured to obtain the maximum negative polarization (Vmax). By setting up the negative polarization <0.6V, the maximum current (Imax) was attained. The charge injection capacity was calculated by integrating current with pulse width, and then averaging by electrode geometry area, which is Qinj=Imax*pulse width/area. The power consumption (mainly capacitive power consumption here) was estimated by Imax*Vmax/2. The impedance data was normalized to the same area of the electrodes. As the characteristics of the electrode (A) and the control electrode (B) are maintained essentially the same but for the surface topography and/or normalized to account for minor variation, it can be deduced that the increased performance by the electrode (A) was directly correlated to the lay and roughness of the surface topology applied to the electrode (A).

TABLE 1

|  | Area (mm$^2$) | Qinj/phase (μC) | Qinj (μC/cm$^2$) | Max current for PW = 400 μs (mA) | Capacitance Power Consumption (mW) for PW = 400 μs & I = 2 mA |
|---|---|---|---|---|---|
| Electrode (A) | 6.48 | 4390 | 76.14 | 12.24 | 0.10 |
| Control electrode (B) | 4.00 | 1.07 | 26.80 | 2.68 | 0.49 |

Figure 5A:
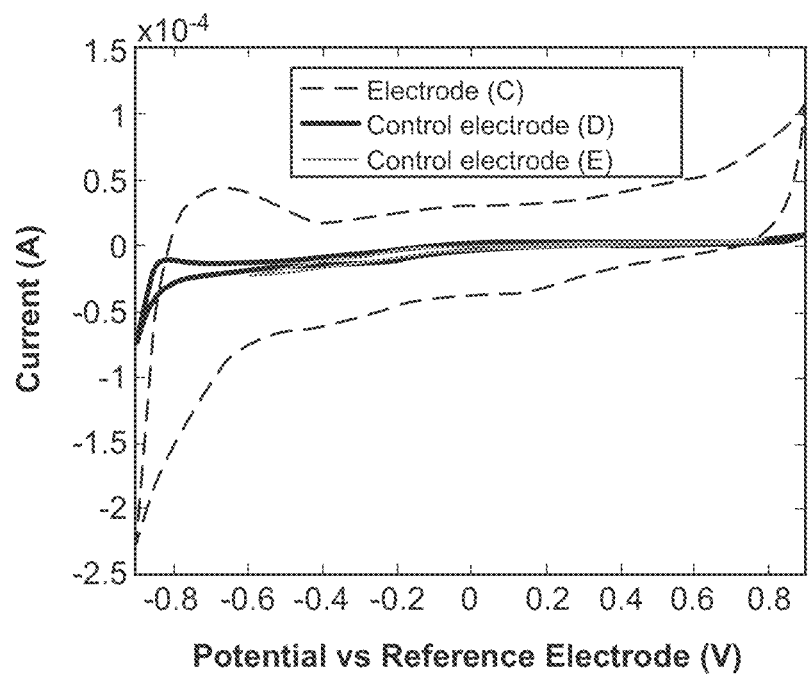
FIGS. 5A and 5B show performance characteristics for the electrode (C), the control electrode (D), and the control electrode (E) in accordance with various embodiments.
Figure 5B:
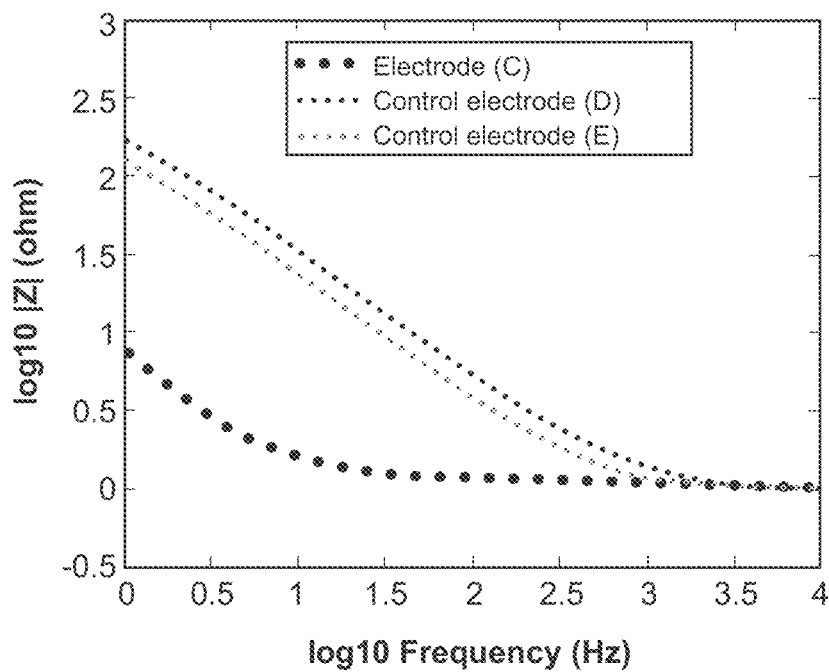

EXAMPLE 2: The performance of an embodiment of an electrode (C) was evaluated versus a control electrode (D) and a control electrode (E). The electrode (C) was manufactured in accordance with the processes described with respect to FIG. 4. The electrode (C) comprised: (i) an interface surface that has an area of 5.70 mm$^2$, and (ii) an alloy comprising platinum and iridium. The interface surface had a surface topography comprising: (i) a horizontal stripe pattern, and (ii) a surface roughness having a $R_a$ of about 1.4 μm. The control electrode (D) comprised: (i) an interface surface that had an area of 4.60 mm$^2$, and (ii) an alloy comprising platinum and iridium. The interface surface had a surface topography comprising: (i) substantially a flat plane, and (ii) a surface roughness having a $R_a$ of about 0.1 μm. The control electrode (E) comprised: (i) an interface surface that had an area of 4.00 mm$^2$, and (ii) an alloy comprising platinum and iridium. The interface surface had a surface topography comprising: (i) substantially a flat plane, and (ii) a surface roughness having a $R_a$ of about 0.6 μm. As shown in Table 2, the electrode (C) outperformed the control electrode (D) and control electrode (E). In particular, the electrode (C) showed a higher charge injection density while maintaining low impedance, and consequently low power consumption, as compared to the control electrode (D) and control electrode (E). FIGS. 5A and 5B show performance characteristics for the electrode (C), the control electrode (D), and the control electrode (E). The maximum current, the injection capacity, and the power consumption were obtained as described with respect to Table 1. The impedance data was normalized to the same area of the electrodes. As the characteristics of the electrode (C), the control electrode (D), and the control electrode (E) where maintained essentially the same but for the surface topography and/or normalized to account for minor variation, it can be deduced that the increased performance by the electrode (C) was directly correlated to the lay and roughness of the surface topology applied to the electrode (C).

TABLE 2

| | Area (mm$^2$) | Qinj/ phase (μC) | Qinj (μC/cm$^2$) | Max current for PW = 400 μs (mA) | Capacitance Power Consumption (mW) for PW = 400 μs & I = 2 mA |
|---|---|---|---|---|---|
| Electrode (C) | 5.70 | 5.37 | 94.20 | 13.42 | 0.64 |
| Control electrode (D) | 4.60 | 0.50 | 10.80 | 1.24 | 1.78 |
| Control electrode (E) | 4.00 | 1.07 | 26.80 | 2.68 | 1.88 |

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A electrode comprising a base body comprising: (i) an interface surface that has an area of less than 50 mm$^2$, and (ii) an alloy comprising platinum and iridium, wherein the interface surface has a surface topography comprising: (i) an artificial pattern, and (ii) a surface roughness having an arithmetical mean height ($R_a$) of greater than 0.8 μm, the electrode comprising a charge injection capacity (Qinj) of greater than 50 μC/cm$^2$.

2. The electrode of claim 1, wherein the artificial pattern comprises a plurality of trenches.

3. The electrode of claim 2, wherein a pitch between each trench of the plurality of trenches is between 5 μm and 100 μm.

4. The electrode of claim 2, wherein each trench of the plurality of trenches has a depth between 2 μm and 50 μm.

5. The electrode of claim 1, wherein the $R_a$ is between 1.8 μm and 50 μm.

6. The electrode of claim 1, wherein the surface roughness has a maximum profile valley depth ($R_v$) of greater than 1.2 μm and a maximum profile peak height ($R_p$) of greater than 1.2 μm.

7. The electrode of claim 6, wherein the $R_v$ is between 2.1 μm and 4.5 μm.

8. The electrode of claim 6, wherein the $R_p$ is between 2.1 μm and 4.5 μm.

9. The electrode of claim 1, wherein the surface roughness has a total profile height ($R_t$) of between 4.2 μm and 8.5 μm.

10. The electrode of claim 1, further comprising a maximum current of greater than 5.0 mA.

11. The electrode of claim 1, further comprising a maximum power consumption of less than 1.0 mW.

12. A medical device comprising:
   an implantable neurostimulator including:
      a housing;
      one or more feedthroughs that pass through the housing; and
      an electronics module within the housing and connected to the one or more feedthroughs; and
   a lead assembly including:
      a lead body including a conductor material;
      a lead connector that connects the conductor material to the one or more feedthroughs; and
      an electrode connected to the conductor material, wherein the electrode comprises: (i) an interface surface that has an area of less than 50 mm$^2$, and (ii) an alloy comprising platinum and iridium, wherein the interface surface has a surface topography comprising: (i) an artificial pattern, and (ii) a surface roughness having an arithmetical mean height ($R_a$) of greater than 0.8 μm, the electrode comprising a charge injection capacity (Qinj) of greater than 50 μC/cm$^2$.

13. The medical device of claim 12, wherein the artificial pattern comprises a plurality of trenches.

14. The medical device of claim 13, wherein each trench of the plurality of trenches has a depth between 2 μm and 50 μm.

15. The medical device of claim 12, wherein the $R_a$ is between 1.8 μm and 50 μm.

16. The medical device of claim 15, wherein the surface roughness has a maximum profile valley depth ($R_v$) between 2.1 μm and 4.5 μm, a maximum profile peak height ($R_p$) between 2.1 μm and 4.5 μm, and a total profile height ($R_t$) of between 4.2 μm and 8.5 μm.

17. A method of manufacturing an electrode, comprising:
   obtaining a base body comprising (i) an interface surface that has an area of less than 50 mm$^2$, and (ii) an alloy comprising platinum and iridium; and
   surface texturing, using a laser device, at least a portion of the interface surface to create a surface topography comprising: (i) an artificial pattern, and (ii) a surface roughness having an arithmetical mean height ($R_a$) of greater than 0.8 μm,
   wherein the electrode comprises a charge injection capacity (Qinj) of greater than 50 μC/cm$^2$.

18. The method of claim 17, wherein the $R_a$ is between 1.8 μm and 50 μm.

19. The method of claim 17, wherein the surface roughness has a maximum profile valley depth ($R_v$) between 2.1 μm and 4.5 μm, a maximum profile peak height ($R_p$) between 2.1 μm and 4.5 μm, and a total profile height ($R_t$) of between 4.2 μm and 8.5 μm.

* * * * *